(12) United States Patent
Yamashita et al.

(10) Patent No.: US 10,792,475 B2
(45) Date of Patent: Oct. 6, 2020

(54) MEDICAL TUBE AND MEDICAL DEVICE

(71) Applicant: TERUMO KABUSHIKI KAISHA, Shibuya-ku, Tokyo (JP)

(72) Inventors: Yasunori Yamashita, Fujinomiya (JP); Yuuki Sakaguchi, Fujinomiya (JP); Yuusuke Sekine, Chigasaki (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 248 days.

(21) Appl. No.: 15/670,455

(22) Filed: Aug. 7, 2017

(65) Prior Publication Data

US 2018/0050177 A1 Feb. 22, 2018

(30) Foreign Application Priority Data

Aug. 18, 2016 (JP) ................................ 2016-160596

(51) Int. Cl.
*A61M 25/09* (2006.01)
*A61M 25/00* (2006.01)
(Continued)

(52) U.S. Cl.
CPC .............. *A61M 25/09* (2013.01); *A61B 8/12* (2013.01); *A61B 8/445* (2013.01); *A61B 34/00* (2016.02);
(Continued)

(58) Field of Classification Search
CPC .......... A61M 25/0068; A61M 25/0102; A61M 25/09; A61M 2025/0063; A61M 2025/09175; A61M 25/0097; A61M 39/10; A61M 2025/0008; A61M 2025/09116; A61M 25/008; A61B 8/445; A61B 2017/00398; A61B 2090/3784; A61B 2090/3966; A61B 34/00; A61B 8/12
See application file for complete search history.

(56) References Cited

U.S. PATENT DOCUMENTS

| 5,443,457 A | | 8/1995 | Ginn et al. | |
| 5,771,895 A | * | 6/1998 | Slager | A61B 5/02007 128/916 |
| 6,770,066 B1 | * | 8/2004 | Weaver | A61M 25/0026 604/508 |
| 2010/0256487 A1 | * | 10/2010 | Hawkins | A61M 25/0028 600/434 |

(Continued)

FOREIGN PATENT DOCUMENTS

| JP | H02-063859 U | 5/1990 |
| JP | H09-225037 A | 9/1997 |

(Continued)

OTHER PUBLICATIONS

Office Action (Notice of Reasons for Refusal) dated Mar. 3, 2020, by the Japanese Patent Office in corresponding Japanese Patent Application No. 2016-160596 and an English Translation of the Office Action. (8 pages).

*Primary Examiner* — Christine H Matthews
*Assistant Examiner* — Joshua Daryl D Lannu
(74) *Attorney, Agent, or Firm* — Buchanan Ingersoll & Rooney PC

(57) ABSTRACT

A medical tube includes a connection portion that is removably attached to an end of a catheter including a guide wire lumen through which a guide wire is inserted and a tube main body that includes a lumen through which the guide wire is inserted. The lumen communicates with the guide wire lumen while being attached to the end of the catheter through the connection portion.

15 Claims, 13 Drawing Sheets

(51) Int. Cl.
*A61M 25/01* (2006.01)
*A61B 34/00* (2016.01)
*A61B 8/12* (2006.01)
*A61B 8/00* (2006.01)
*A61B 90/00* (2016.01)
*A61B 17/00* (2006.01)
*A61M 39/10* (2006.01)

(52) U.S. Cl.
CPC ...... *A61M 25/008* (2013.01); *A61M 25/0097* (2013.01); *A61M 25/0102* (2013.01); *A61B 2017/00398* (2013.01); *A61B 2090/3784* (2016.02); *A61B 2090/3966* (2016.02); *A61M 25/0068* (2013.01); *A61M 39/10* (2013.01); *A61M 2025/0008* (2013.01); *A61M 2025/0063* (2013.01); *A61M 2025/09116* (2013.01); *A61M 2025/09175* (2013.01)

(56) References Cited

U.S. PATENT DOCUMENTS

| | | | |
|---|---|---|---|
| 2014/0309533 A1* | 10/2014 | Yamashita | A61M 25/0009 600/463 |
| 2015/0314104 A1* | 11/2015 | Almansouri | A61M 25/0606 128/845 |
| 2016/0220741 A1 | 8/2016 | Garrison et al. | |

FOREIGN PATENT DOCUMENTS

| JP | 10-500584 A | 1/1998 |
|----|-------------|--------|
| JP | H10-118192 A | 5/1998 |
| JP | 2002-360703 A | 12/2002 |
| JP | 2004-049583 A | 2/2004 |
| JP | 2007-236628 A | 9/2007 |

\* cited by examiner

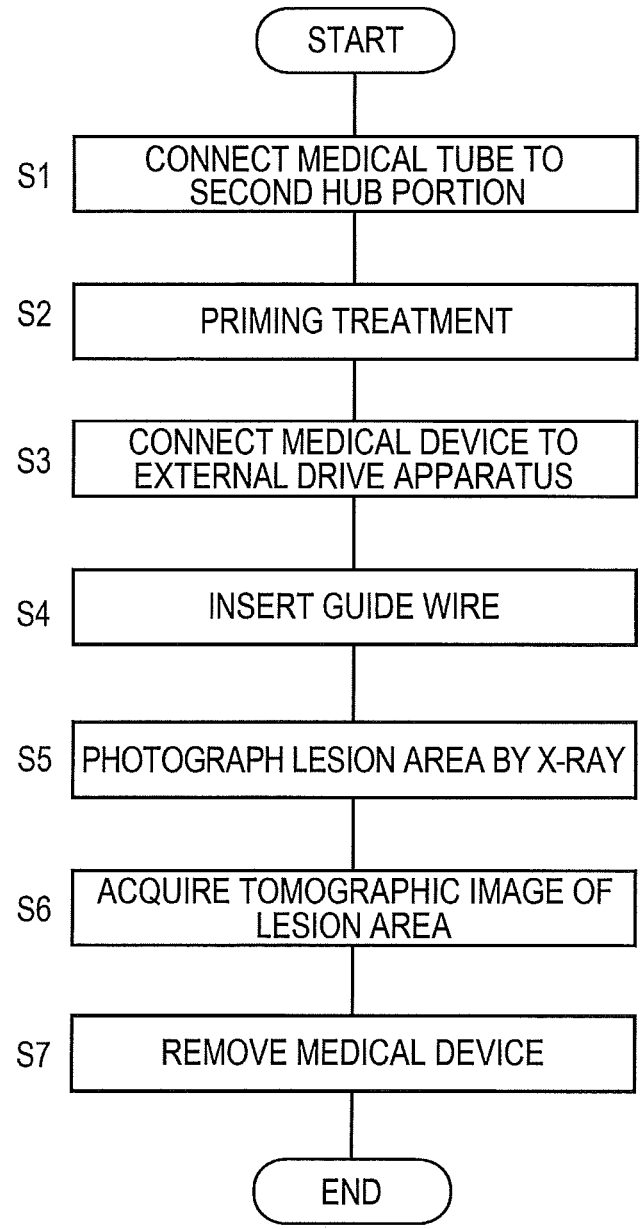

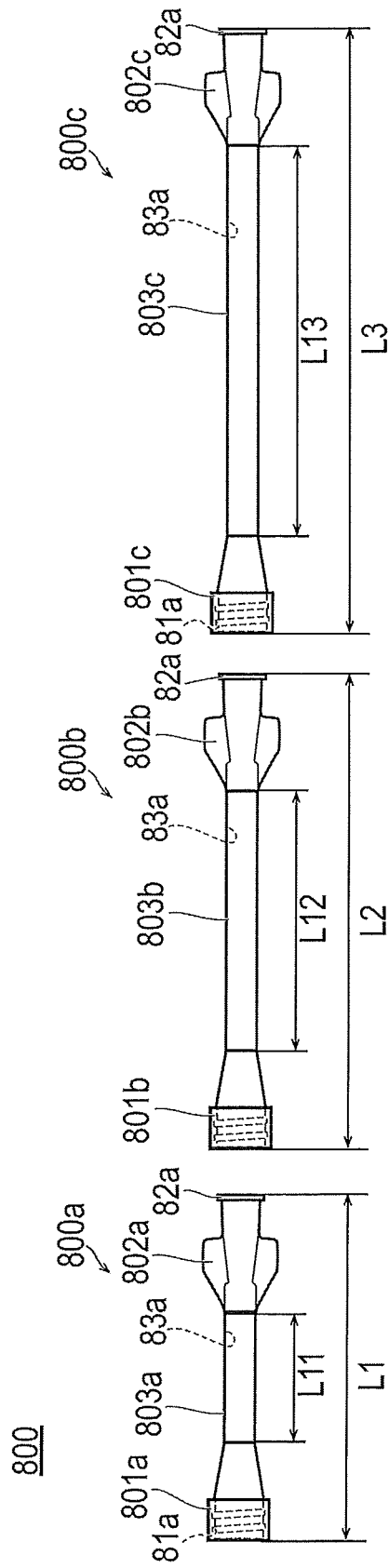
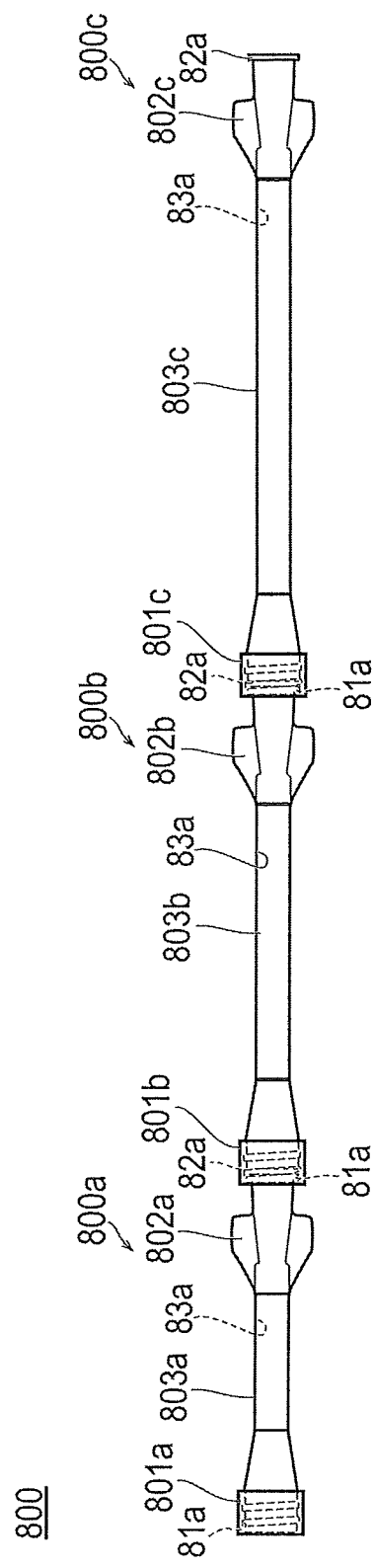
Fig. 9(A)
Fig. 9(B)

810

810

MEDICAL TUBE AND MEDICAL DEVICE

CROSS-REFERENCES TO RELATED APPLICATIONS

This application is based on and claims priority to Japanese Application No. 2016-160596 filed on Aug. 18, 2016, the entire content of which is incorporated herein by reference.

TECHNICAL FIELD

The present invention generally relates to a medical tube and a medical device.

BACKGROUND DISCUSSION

Hitherto, various treatment methods have been known as a method of treating a lesion of a body lumen. For example, Japanese Application Publication No. 10-500584 discloses a method of performing a predetermined diagnosis or treatment on a lesion area by first inserting a guide wire to the lesion area and then inserting a medical device including a guide wire lumen into a body lumen along the guide wire.

SUMMARY

In general, since a position for operating the medical device is determined by the length of the catheter of the medical device, the position cannot be adjusted flexibly. For this reason, since there is a need to perform a work at a position where the medical device can be operated by an operator, situations arise in which a burden on the operator increases when the operator performs a work in an unreasonable posture.

Further, when the guide wire is inserted through the body lumen or the lesion area is diagnosed or treated by the medical device, work is performed while confirming the position of the guide wire or the medical device in the body lumen on the basis of an angiographic image captured by irradiating an X-ray from the outside of the body. Since the position where the medical device can be operated is limited as described above, there is a possibility that an exposure amount to the operator may increase when the operator performs work (an operation) at a position where the amount of irradiation of the X-ray is relatively high.

The medical tube and a medical device disclosed here improve workability while reducing the operator's exposure amount.

A medical tube includes: a connection portion that is removably attached to an end of a catheter including a guide wire lumen through which a guide wire is inserted; and a tube main body that includes a lumen through which the guide wire is inserted. The lumen communicates with the guide wire lumen while being attached to the end of the catheter through the connection portion.

A medical device is a medical device for acquiring an image while being inserted into a body lumen. The medical device includes: an imaging sheath that includes an imaging lumen into which a rotatable drive shaft is inserted; a guide wire sheath that includes a guide wire lumen which is disposed in parallel to the imaging lumen and through which a guide wire is inserted; a hub portion that is connected to a proximal end of the guide wire sheath; an imaging unit that is fixed to a distal end of the drive shaft and is able to acquire image information; and a medical tube that includes a connection portion removably attached to the hub portion and a tube main body including a lumen through which the guide wire is inserted. The lumen communicates with the guide wire lumen while the medical tube is attached to the hub portion through the connection portion.

According to the medical tube and the medical device with the above-described configuration, it is possible to flexibly adjust a working position of an operator who operates the guide wire by the medical tube. Accordingly, the workability of the operator can be improved. Further, since the working position is adjusted by the medical tube, the operator can perform a work at a position where the amount of irradiation of the X-ray is relatively low when a patient is photographed by an X-ray. For this reason, the amount of exposure of the X-ray to the operator can be reduced.

According to another aspect, a method comprises introducing a guide wire into an open distal end of a medical device while the guide wire is positioned in a blood vessel and moving the medical device in a distal direction along the guide wire while the guide wire is positioned in the blood vessel so that the medical device is introduced into the blood vessel and the guide wire moves along a guide wire lumen in the medical device. The medical device comprises a hub through which the guide wire lumen passes, wherein the hub includes a hub portion through which the guide wire lumen passes and a proximal end. The medical device also includes a medical tube removably connected to the proximal end of the hub portion, with the medical tube including a lumen that communicates with the guide wire lumen passing through the hub portion. The method also involves advancing the medical device along the guide wire to cause the guide wire to pass through the guide wire lumen in the hub and the hub portion; and further advancing the medical device along the guide wire to cause the guide wire to pass through the lumen in the medical tube so that the guide wire projects proximally beyond a proximal end of the medical tube so that the medical tube is located outside the medical tube.

BRIEF DESCRIPTION OF THE DRAWINGS

FIG. 6 is a flowchart illustrating a diagnosis method using the medical device according to the embodiment.

FIG. 9(A) is a plan view illustrating a medical tube according to a first modified example and FIG. 9(B) is a plan view illustrating a state where a plurality of medical tubes are connected.

DETAILED DESCRIPTION set forth below with reference to the accompanying drawings is a detailed description of an embodiment of a medical tube and medical device representing an example of the inventive medical tube and medical device disclosed here. The following description does not limit the technical scope and the meaning of the terms described in the claims. The illustrated dimensional ratios of the drawings are exaggerated for convenience of explanation and may be different from the actual ratios.

Figure 1:
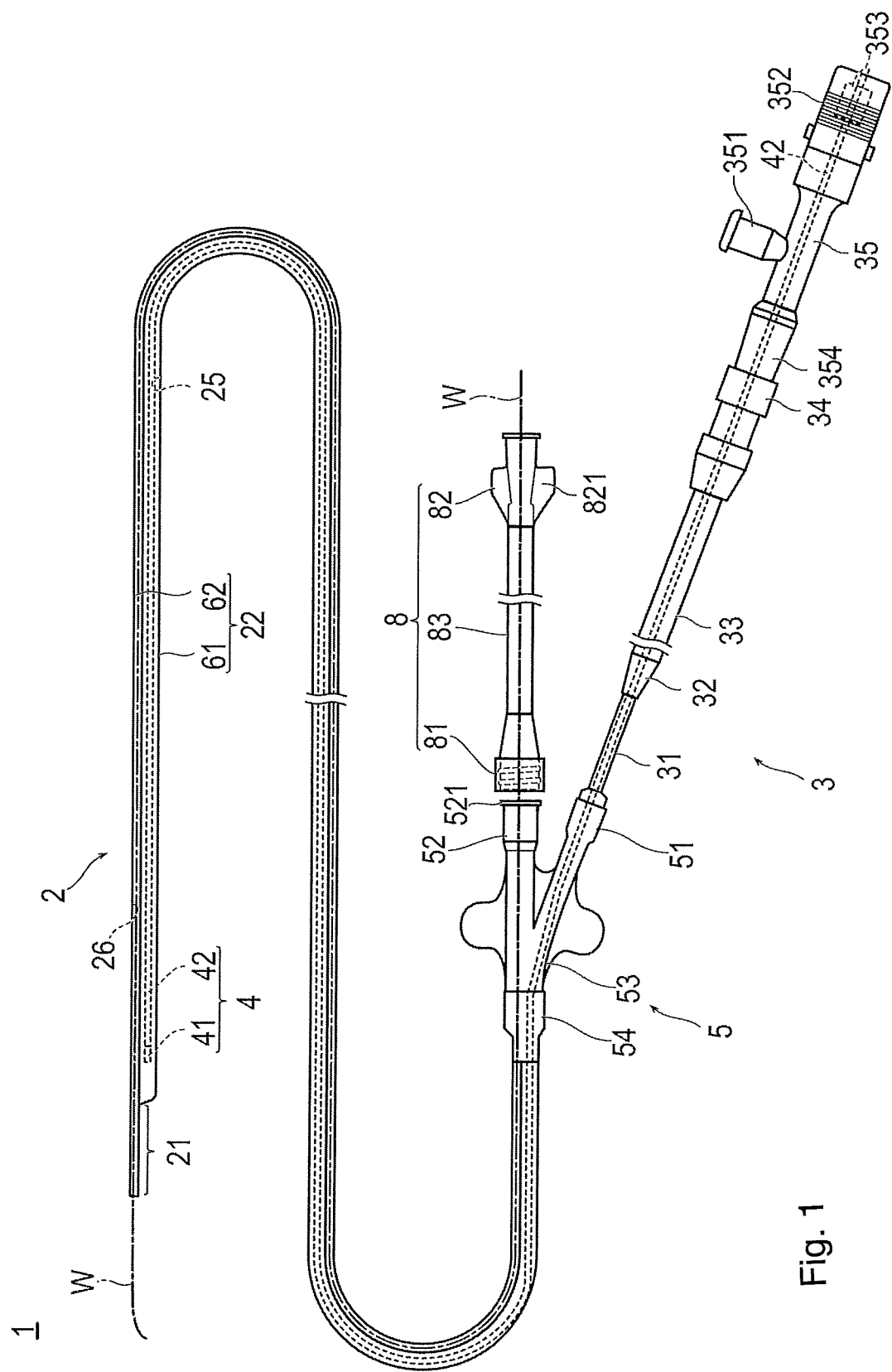
FIG. 1 is a plan view illustrating a medical device according to one embodiment representing an example of the disclosed medical device.
Figure 2:
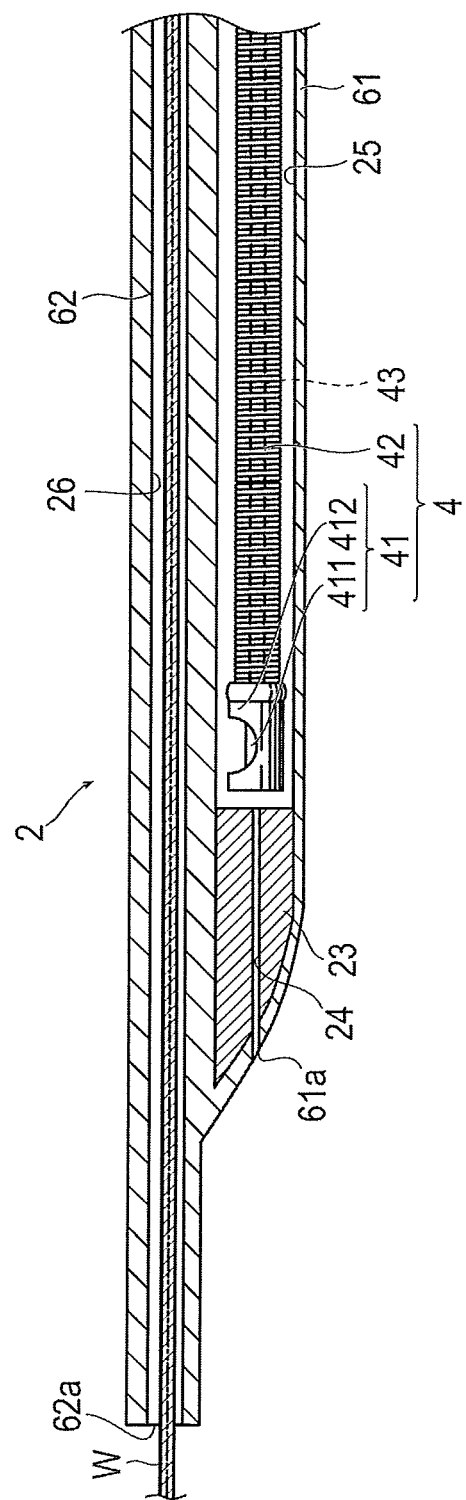
FIG. 2 is a cross-sectional view illustrating a distal portion of the medical device according to the embodiment when taken along the axial direction.

A medical device 1 is, as illustrated in FIGS. 1 and 2, an ultrasound catheter which internally accommodates an imaging core 4 for an ultrasound diagnosis and is configured to be inserted into a body lumen. The medical device 1 is connected to an external drive apparatus 7 (see FIG. 5) which holds the medical device 1 and drives or moves the imaging core 4 and is used to diagnose the inside of a body lumen such as a blood vessel. In the description which follows, the side to be inserted into a lumen of a living body is referred to as a "distal end" or a "distal side" and the proximal side to be operated will be referred to as a "proximal end" or a "proximal side".

The medical device 1 includes, as illustrated in FIG. 1, an elongated shaft portion 2 which is inserted into a lumen, an operation unit 3 which operates the imaging core 4, the imaging core 4 which transmits and receives ultrasound waves to tissue inside a lumen, a hub 5 through which the imaging core 4 passes and which is located at the proximal side in relation to the shaft portion 2, and a medical tube 8.

The shaft portion 2 includes a shaft distal portion 21 and a shaft main body portion 22 which is disposed at the proximal side of the shaft distal portion 21.

The shaft distal portion 21 is provided with a guide wire lumen 26 into which a guide wire W is inserted. In the description which follows, a direction following the longitudinal directions of the shaft portion 2 and the guide wire W will be referred to as an "axial direction".

The shaft main body portion 22 is provided with an imaging lumen 25 into which the imaging core 4 is inserted and a guide wire lumen 26 into which the guide wire W is inserted. The guide wire lumen 26 is disposed substantially in parallel to the imaging lumen 25. The guide wire lumen 26 is formed to communicate from the shaft distal portion 21 to the shaft main body portion 22. That is, the guide wire lumen 26 extends from the shaft distal portion 21 to the shaft main body portion 22. The cross-sectional shapes of the imaging lumen 25 and the guide wire lumen 26 are not particularly limited, but may be, for example, substantially circular.

The guide wire W used in the medical device 1 of the embodiment is an elongated body which has flexibility and has a substantially constant outer diameter throughout the entire length. The cross-sectional shape of the guide wire W is not particularly limited, but may be, for example, substantially circular.

The guide wire W can be observed by an angiographic image obtained by photographing the body lumen from the outside of the body through X-rays. A material forming the guide wire W is not particularly limited as long as an observation can be performed by the angiographic image and, for example, metal such as stainless steel, spring steel, titanium, tungsten, tantalum, and super elastic alloy like nickel-titanium alloy can be used.

The shaft portion 2 is formed by thermally fusing (or bonding) an imaging sheath 61 provided with the imaging lumen 25 and a guide wire sheath 62 provided with the guide wire lumen 26.

As illustrated in FIG. 2, the imaging sheath 61 includes a distal end opening portion 61a, and the guide wire sheath 62 includes a distal end opening portion 62a. The distal portion of the imaging sheath 61 is provided with a reinforcement tube 23 for rigidly bonding and supporting the guide wire sheath 62. The reinforcement tube 23 is a cylindrical body or tubular body provided with a communication hole 24 communicating with the distal end opening portion 61a. The reinforcement tube 23 is thermally fused (or bonded) to the imaging sheath 61 by a relatively rigid material (rigid so as to reinforce to firmly bond and support).

Figure 3:
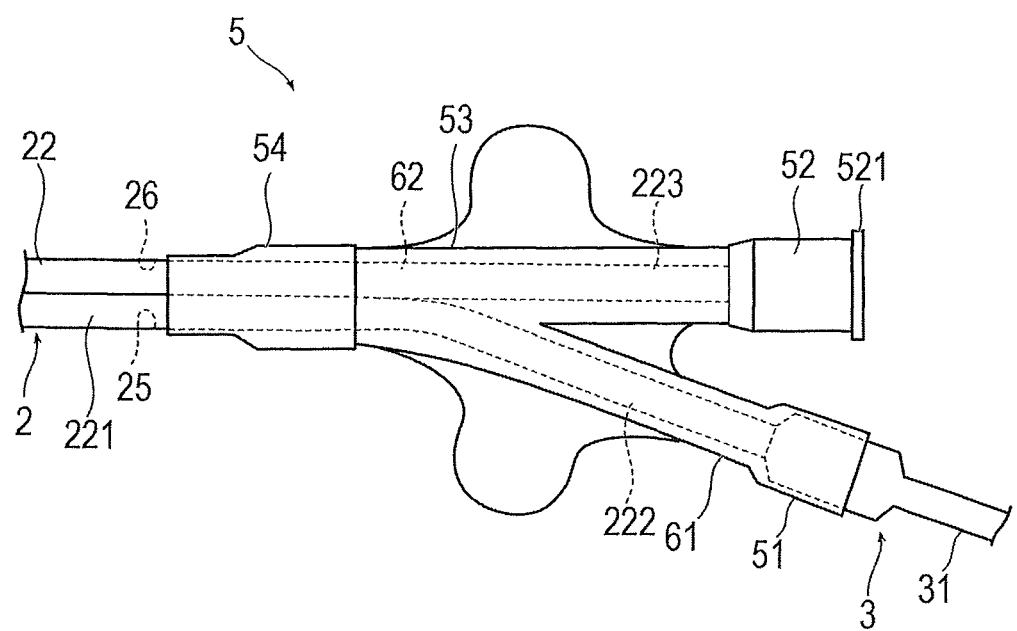
FIG. 3 is a plan view illustrating a hub of the medical device according to the embodiment.

The shaft main body portion 22 includes, as illustrated in FIG. 3, a shaft intermediate portion 221 which has the imaging lumen 25 and the guide wire lumen 26 formed in parallel at the distal side and a first shaft proximal portion 222 and a second shaft proximal portion 223 which extend away from and are branched from the shaft intermediate portion 221 toward the proximal end. The imaging lumen 25 is formed inside the first shaft proximal portion 222 and the guide wire lumen 26 is formed inside the second shaft proximal portion 223. The outer diameter and the inner diameter of the shaft main body portion 22 may be different (i.e., may vary) depending on the position in the axial direction. For example, when the outer diameter and the inner diameter are decreased in a taper shape from the proximal side toward the distal side so that an extreme change in physical property does not occur, it is possible to suppress the occurrence of kinking while realizing high pushability and passability.

The length of the shaft portion 2 in the axial direction is not particularly limited and may be, for example, 600 mm to 2000 mm. In a case where the medical device 1 is used for a procedure for a lower limb, that is, a femoral artery puncture, the axial length of the shaft portion 2 can be shorter than the medical device used for a heart procedure, the latter of which may be in a range, for example, from 600 mm to 1200 mm.

The shaft distal portion 21 and the shaft main body portion 22 are formed of a flexible material, and the material thereof is not particularly limited. For example, various thermoplastic elastomers such as styrene type, polyolefin type, polyurethane type, polyester type, polyimide type, polyimide type, polybutadiene type, trans polyisoprene type, fluoro rubber type, and chlorinated polyethylene type can be exemplified and one or a combination of two or more thereof (polymer alloy, polymer blend, laminate, and the like) can be employed. Additionally, it is desirable to form the imaging sheath 61 provided with the imaging lumen 25 by a material with high ultrasound transmittance.

In the operation unit 3, as illustrated in FIG. 3, a distal portion is connected to the first shaft proximal portion 222 through a first hub portion 51 to be described later and a proximal portion is connected to the external drive apparatus 7 in order to operate the imaging core 4. The operation unit 3 includes, as illustrated in FIG. 1, a flexible portion 31 which is connected to the first hub portion 51, a third anti-kink protector 32, a tubular member 33 that is connected to the proximal portion of the flexible portion 31, a unit connector 34 which is connected to the proximal portion of the tubular member 33, and an operation proximal portion 35 which is connected to the proximal portion of the unit connector 34.

The flexible portion 31 is more flexible than the tubular member 33. Since the medical device 1 is pulled toward the proximal side or in the proximal direction along the axial direction of the guide wire W when the medical device 1 is separated from the guide wire W, for example, while the position of the external drive apparatus 7 is fixed, the operation unit 3 extending in a direction intersecting the axial direction is deformed. At this time, since the flexible portion 31 connected to the first hub portion 51 is flexibly deformed, it is possible to prevent damage to the connection portion between the operation unit 3 and the first hub portion 51. Further, the outer diameter of the flexible portion 31 is smaller than that of the tubular member 33. Accordingly, the flexibility can be further improved.

The flexible portion 31 can be formed of polyetheretherketone (PEEK) or the same material as those of the shaft distal portion 21 and the shaft main body portion 22.

The third anti-kink protector 32 is disposed at the connection portion between the flexible portion 31 and the tubular member 33 and suppresses kinking of the flexible portion 31 and the tubular member 33.

The inner lumens of the flexible portion 31 and the tubular member 33 communicate with the imaging lumen 25 and a drive shaft 42 is inserted therethrough.

The unit connector 34 is inserted so that the proximal portion of the tubular member 33 is fitted into the unit connector 34. The unit connector 34 is connectable to the holding portion 73 (see FIG. 5) of the external drive apparatus 7.

The operation proximal portion 35 holds the drive shaft 42. The operation proximal portion 35 includes a port 351, a joint 352, a hub side connector 353 connected to the proximal portion of the drive shaft 42, and a second anti-kink protector 354.

The port 351 communicates with the imaging lumen 25. The port 351 is connected to a priming syringe or a Y-connector and is used to supply a fluid such as a priming solution to the imaging lumen 25.

The joint 352 includes an opening formed at the proximal side, and the hub side connector 353 is disposed in the opening. The hub side connector 353 is connectable to a drive side connector 711 (see FIG. 5) of the external drive apparatus 7 from the proximal side of the joint 352, and the external drive apparatus 7 and the hub side connector 353 are mechanically and electrically connected by the connection.

One end of a signal line 43 (see FIG. 2) is connected to the hub side connector 353 and the signal line 43 passes through the drive shaft 42 so that the other end of the signal line 43 is connected to an oscillator unit 41 as illustrated in FIG. 2. By a signal which is transmitted from the external drive apparatus 7 to the oscillator unit 41 through the drive side connector 711, the hub side connector 353, and the signal line 43, an ultrasound wave is emitted from the oscillator unit 41. Further, a signal which is detected by the oscillator unit 41 while receiving an ultrasound wave is transmitted to the external drive apparatus 7 through the signal line 43, the hub side connector 353, and the drive side connector 711.

The second anti-kink protector 354 is disposed in the periphery of the tubular member 33 and the operation proximal portion 35 to suppress kinking of the tubular member 33.

The imaging core 4 is disposed inside the imaging lumen 25 of the shaft portion 2 as illustrated in FIG. 2. The imaging core 4 includes the oscillator unit 41 (an imaging unit) which transmits an ultrasound wave from a lumen to a biological tissue and receives the ultrasound wave therefrom, and a drive shaft 42 which rotates the oscillator unit 41 and whose distal end is connected to the oscillator unit 41. The oscillator unit 41 includes an ultrasound transducer 411 which transmits and receives an ultrasound wave and a housing 412 which accommodates the ultrasound transducer 411.

The oscillator unit 41 can be observed by an angiographic image. Although the material of the housing 412 is not limited, it is desirable to include metal such as gold, platinum, platinum alloy, and tungsten alloy or an X-ray contrasting material such as barium sulfate, bismuth oxide, and tungsten so that the housing serves as an X-ray contrasting portion. Further, an X-ray contrast marker may be separately provided in the vicinity of the housing 412.

The drive shaft 42 is flexible, is able to transmit rotational power generated in the operation unit 3 to the oscillator unit 41, and is formed as, for example, a multilayered coil-shaped pipe body or cylindrical body such as a three-layer coil having alternate right and left winding directions. When the drive shaft 42 transmits rotational power, the oscillator unit 41 rotates and thus a lesion area inside a body lumen such as a blood vessel can be observed in the circumferential direction. Further, the signal line 43 which transmits a signal detected by the oscillator unit 41 to the operation unit 3 passes through the drive shaft 42.

The hub 5 includes, as illustrated in FIG. 3, the first hub portion 51 which is air-tightly and liquid-tightly connected to the first shaft proximal portion 222, a second hub portion 52 (the end of the catheter) which is air-tightly and liquid-tightly connected to the second shaft proximal portion 223, a hub main body portion 53 which is connected to the first hub portion 51 and the second hub portion 52, and a first anti-kink protector 54. The first hub portion 51, the second hub portion 52, and the hub main body portion 53 are integrally formed in one piece.

As illustrated in FIGS. 1 and 3, the first hub portion 51 is connected by thermal fusing or bonding while the distal portion of the flexible portion 31 is fitted from the proximal side of the first hub portion 51 and the first shaft proximal portion 222 is inserted from the distal side of the first hub portion 51. Thus, the saline solution (saline) and the drive shaft 42 passing through the flexible portion 31 are movable toward the imaging lumen 25 through the first hub portion 51.

The second hub portion 52 is air-tightly and liquid-tightly connected by thermal fusing or bonding while the second shaft proximal portion 223 is inserted from the distal side of the second hub portion 52. The second hub portion 52 communicates with the guide wire lumen 26 and the guide wire W can pass therethrough. The outer peripheral surface of the second hub portion 52 is provided with a male screw portion 521 (male connector) having a screw thread protruding in an annular shape. The male screw portion 521 can be threaded into a female screw portion 81a (female connector) of a first connection portion 81 of the medical tube 8 to be described later (see FIG. 4(B)).

As illustrated in FIG. 3, the hub main body portion 53 covers the outer peripheral surfaces of the first shaft proximal portion 222 and the second shaft proximal portion 223 respectively connected to the first hub portion 51 and the second hub portion 52.

A portion which is branched into the first shaft proximal portion 222 and the second shaft proximal portion 223 from the shaft intermediate portion 221 toward the proximal end is disposed inside the hub main body portion 53. For this reason, since the imaging sheath 61 and the guide wire sheath 62 are not bonded to each other, the first shaft proximal portion 222 and the second shaft proximal portion 223 having rigidity smaller than that of the shaft intermediate portion 221 can exhibit high pushability while not being positioned at the outside of the hub main body portion 53.

As illustrated in FIG. 1, the first anti-kink protector 54 surrounds the shaft main body portion 22 drawn from the hub main body portion 53 and the distal portion of the hub main body portion 53 to suppress kinking of the shaft main body portion 22.

Materials forming the first hub portion 51, the second hub portion 52, the hub main body portion 53, the tubular member 33, the unit connector 34, and the operation proximal portion 35 are not particularly limited. Examples of such materials include various resins such as polyvinyl chloride, polyethylene, polypropylene, cyclic polyolefin, polystyrene, poly-(4-methylpentene-1), polycarbonate, acrylic resin, acrylonitrile-butadiene-styrene copolymer, polyester such as polyethylene terephthalate and polyethylene naphthalate, butadiene-styrene copolymer, and polyamide (for example, nylon 6, nylon 6·6 (Nylon-6,6 or Nylon-6/6), nylon 6·10 (Nylon-6,10 or Nylon-6/10), and nylon 12).

In addition, the configuration of the hub 5 is not limited to the above-described configuration and, for example, a casing having a split structure may be used to cover the proximal portion of the shaft intermediate portion 221 and the outer peripheral surfaces of the first shaft proximal portion 222 and the second shaft proximal portion 223.

Figure 4A:
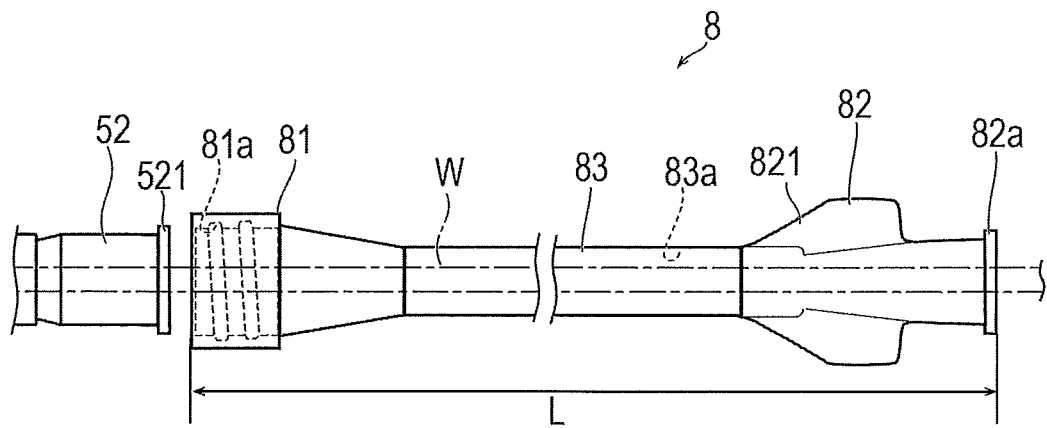
FIG. 4(A) is a plan view illustrating a medical tube according to the embodiment and FIG. 4(B) is a plan view illustrating a state where a second hub portion is connected to the medical tube.

The medical tube 8 includes, as illustrated in FIG. 4(A), the first connection portion 81, a second connection portion 82, and a tube main body 83 which is disposed between the first connection portion 81 and the second connection portion 82.

Figure 4B:
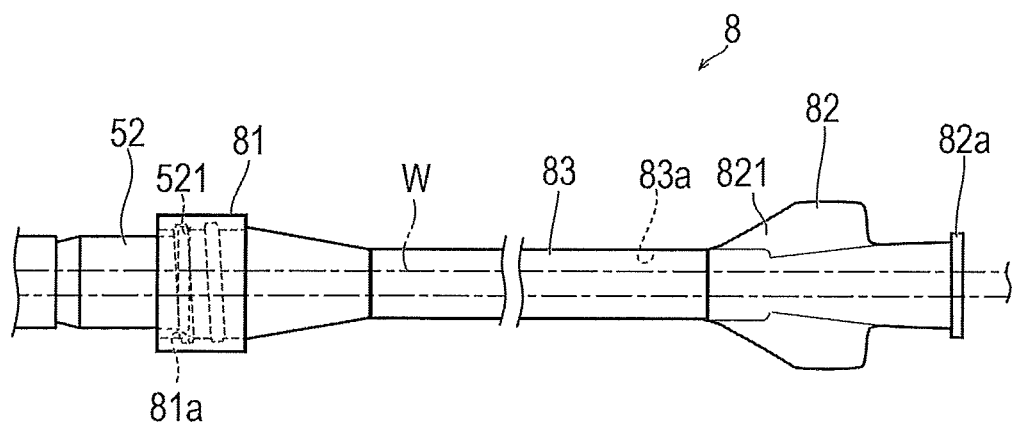

The first connection portion 81 is air-tightly and liquid-tightly connected to the distal portion of the tube main body 83. The inner peripheral surface of the inner lumen of the first connection portion 81 is provided with the female screw portion 81a having a thread groove. The first connection portion 81 is removably attached to the second hub portion 52 in such a manner that the male screw portion 521 of the second hub portion 52 is threaded into the female screw portion 81a as illustrated in FIG. 4(B).

The second connection portion 82 is air-tightly and liquid-tightly connected to the proximal portion of the tube main body 83. The second connection portion 82 serves as a port for supplying a fluid such as a priming solution to the tube main body 83. The second connection portion 82 includes a male screw portion 82a having a screw thread protruding in an annular shape and threaded into a female screw portion (not illustrated) of a priming syringe or a Y-connector.

The second connection portion 82 includes a blade portion 821 which is widened in a direction intersecting the axial direction. The operator can grip the blade portion 821 when operating the medical tube 8 and so the operability is improved.

The tube main body 83 includes a lumen 83a through which the guide wire W is inserted. The diameter of the lumen 83a is not particularly limited as long as the guide wire W can be pass through the lumen. An example of a diameter of the lumen 83a is 0.3 mm to 1.0 mm.

The length L of the medical tube 8 in the axial direction can be appropriately selected in accordance with the length of the shaft portion 2 or the application of the medical device and can be, for example, 300 mm to 600 mm when the medical device 1 is used for a procedure for a lower limb.

It is desirable to form the first connection portion 81, the second connection portion 82, and the tube main body 83 by the same material and, for example, polyethylene can be used. Due to the same forming material, the first connection portion 81 and the tube main body 83 can be connected by thermal fusing as in the second connection portion 82 and the tube main body 83. Accordingly, since a connection portion is formed without a step or the like, it is possible to suppress the guide wire W from being caught by the connection portion.

Figure 5:
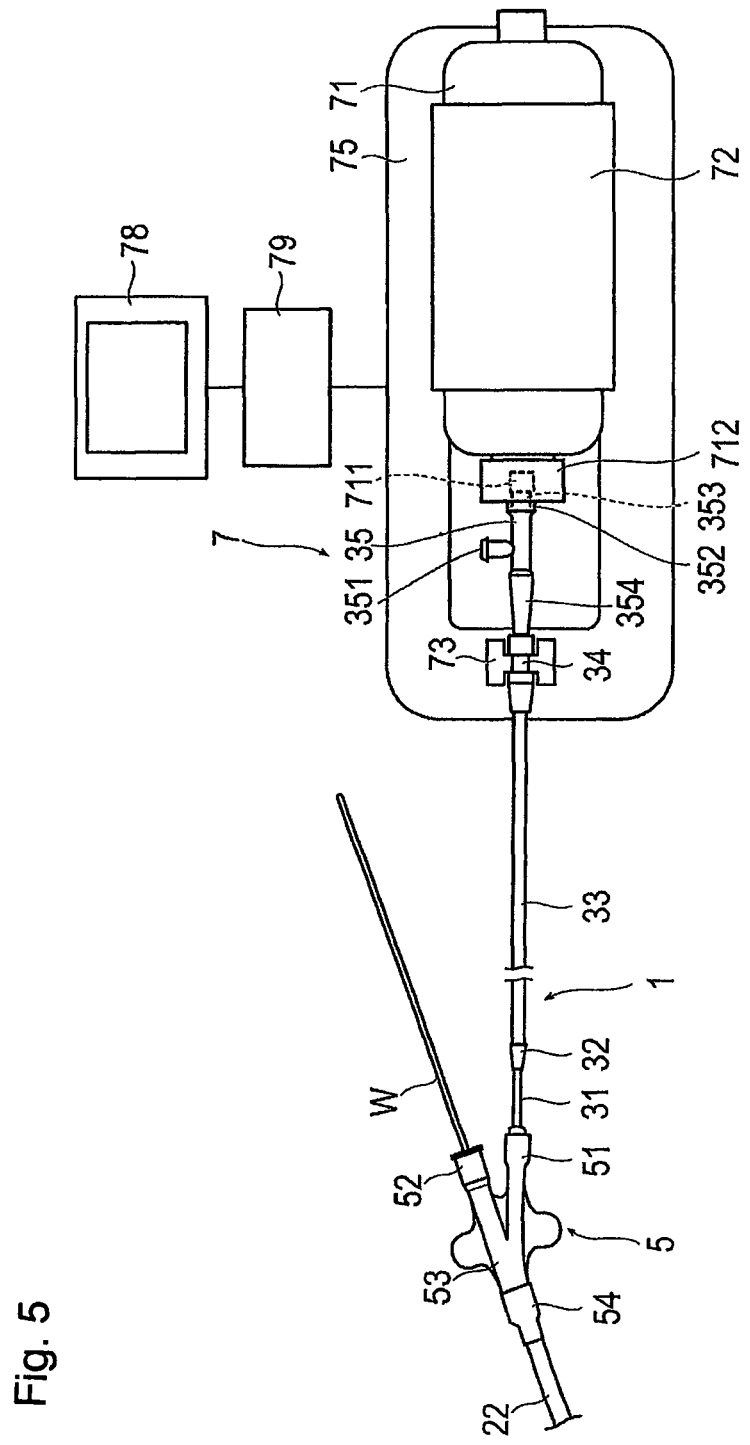
FIG. 5 is a plan view illustrating an external drive apparatus.

The medical device 1 is driven while being connected to the external drive apparatus 7 as illustrated in FIG. 5. The external drive apparatus 7 includes a drive unit 71 which rotates the drive shaft 42 and has an external drive source such as a motor embedded on a base 75, a fixing portion 72 which fixes the drive unit 71 by gripping, and a holding portion 73 which holds a part of the medical device 1 in a fixed manner. The external drive apparatus 7 is connected to a control unit 79 which controls the drive unit 71 and the fixing portion 72 and an image obtained by the oscillator unit 41 is displayed on a display unit 78 connected to the control unit 79.

The drive unit 71 includes a drive side connector 711 to which the hub side connector 353 of the medical device 1 is connectable and a joint connection portion 712 which is connectable to the joint 352 of the medical device 1. Since the joint connection portion 712 is connected to the joint 352, a signal can be transmitted to and received from the oscillator unit 41 and the drive shaft 42 can be rotated.

In the ultrasound scanning (scan) of the medical device 1, the rotation of the motor inside the drive unit 71 is transmitted to the drive shaft 42 to rotate the housing 412 fixed to the distal end of the drive shaft 42. Accordingly, the ultrasound transducer 411 provided in the housing 412 rotates and thus an ultrasound wave which is transmitted and received by the ultrasound transducer 411 can be scanned in the substantially radial direction. Accordingly, it is possible to obtain a tomographic image of 360° for a surrounded tissue body inside a body lumen.

Next, an operation of observing a biological tissue from the inside of a body lumen such as a blood vessel using the medical device 1 according to the embodiment will be described with reference to FIGS. 6 to 8. In the following description, a lesion area which is formed in a blood vessel of a lower limb of the patient P corresponds to an observation area.

First, at step S1, the first connection portion 81 of the medical tube 8 is connected to the second hub portion 52 (see FIG. 4(B)).

Next, at step S2, a priming treatment or priming procedure is performed to charge the medical device 1 with a saline solution. By the priming treatment, an ultrasound wave can be transmitted from the ultrasound transducer 411 and air inside the medical device 1 is removed, thereby preventing air from intruding into a blood vessel.

In order to perform a priming treatment on the imaging lumen 25, a physiological saline is injected through a mechanism including a three-way stopcock and a tube connected to the port 351 of the operation proximal portion 35 by using, for example, a syringe or the like. The injected saline solution passes through the first hub portion 51 from the operation proximal portion 35 and is charged into the imaging lumen 25. Then, the saline solution comes out from the distal end opening portion 61a (see FIG. 2). Accordingly, the charging of the saline solution is confirmed and the priming operation inside the imaging lumen 25 is completed.

In order to perform a priming operation on the guide wire lumen 26, a saline solution is injected through a mechanism including a three-way stopcock and a tube connected to the second connection portion 82 of the medical tube 8 by using, for example, a syringe or the like. The injected saline solution passes through the second hub portion 52 from the medical tube 8 and is charged into the guide wire lumen 26. Then, the saline solution comes out from the distal end opening portion 62a (see FIG. 2). Accordingly, the charging of the saline solution is confirmed and the priming treatment inside the guide wire lumen 26 is completed.

Next, at step S3, as illustrated in FIG. 5, the medical device 1 is connected to the external drive apparatus 7 covered with a sterilized polyethylene bag or the like. That is, the joint 352 of the operation proximal portion 35 of the medical device 1 is connected to the joint connection portion 712 of the drive unit 71. Accordingly, a signal can be transmitted and received between the oscillator unit 41 and the external drive apparatus 7 and the drive shaft 42 can be rotated. Then, when the unit connector 34 is fitted to the holding portion 73, the connection is completed.

Next, at step S4, the guide wire W is inserted into a blood vessel through the guiding sheath S percutaneously inserted into the blood vessel by the Seldinger method. Next, the proximal portion of the guide wire W is inserted into the guide wire lumen 26 through the distal end opening portion 62a.

After the guide wire W is drawn to the proximal side or proximal end from the second connection portion 82 of the medical tube 8, the shaft portion 2 of the medical device 1 is moved forward along the guide wire W and the distal portion of the shaft portion 2 is disposed at the far side (the distal side) in relation to the observed lesion area. That is, the distal portion of the shaft portion 2 is moved past the lesion area so that the distal portion of the shaft portion 2 is positioned distally beyond the lesion area. At this time, since the first hub portion 51 and the second hub portion 52 are directed in different directions, the guide wire W can be operated without the interference with the operation unit 3 or the external drive apparatus 7.

Further, since the guide wire lumen 26 is opened at the second connection portion 82 of the medical tube 8, the guide wire W can be rather easily replaced. For this reason, the medical device 1 can reach a deep portion of a complex portion by properly using the guide wire W having a desired load and a desired shape. That is, the medical device 1 can reach a deep portion of a complex portion by replacing guide wires W and using different guide wires W having a desired load and a desired shape. Further, a contrast agent or a medicine can be supplied to the guide wire lumen 26 through the second connection portion 82 of the medical tube 8 to be discharged from the distal end opening portion 62a into the body.

Next, at step S5, an angiographic image is acquired by photographing a position (a lesion area) provided with the oscillator unit 41 through an X-ray from the outside of the body. By confirming the angiographic image, the position or the posture of the distal portion of the medical device 1 can be checked.

Figure 7A:
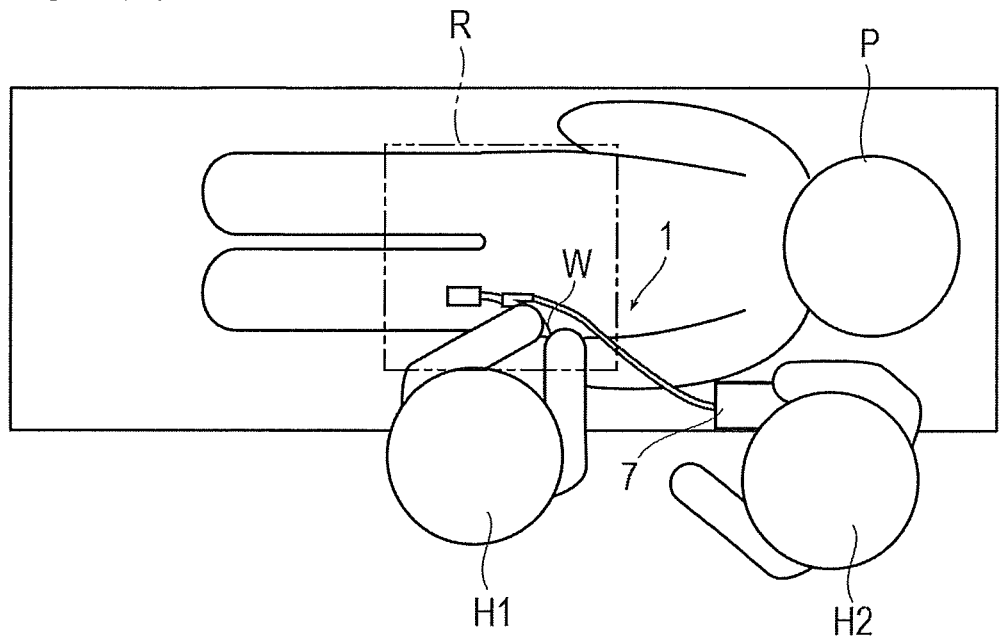
FIG. 7(A) is a diagram schematically illustrating a case where a diagnosis is performed by using a medical device according to a comparative example and FIG. 7(B) is a diagram schematically illustrating a case where a diagnosis is performed by using the medical device according to the embodiment.

In a procedure of treating a lesion area of a lower limb, the distance from a position where an operator H1 of the medical device 1 operates the guide wire W to the lesion area is relatively short compared to a procedure of treating a lesion area of a heart. For this reason, as illustrated in FIG. 7(A), there is a case where the operator H1 works within a range R in which the amount of irradiation of the X-ray is relatively high. Accordingly, there is a possibility that the amount of exposure of the X-ray to the operator H1 may increase.

Figure 7B:
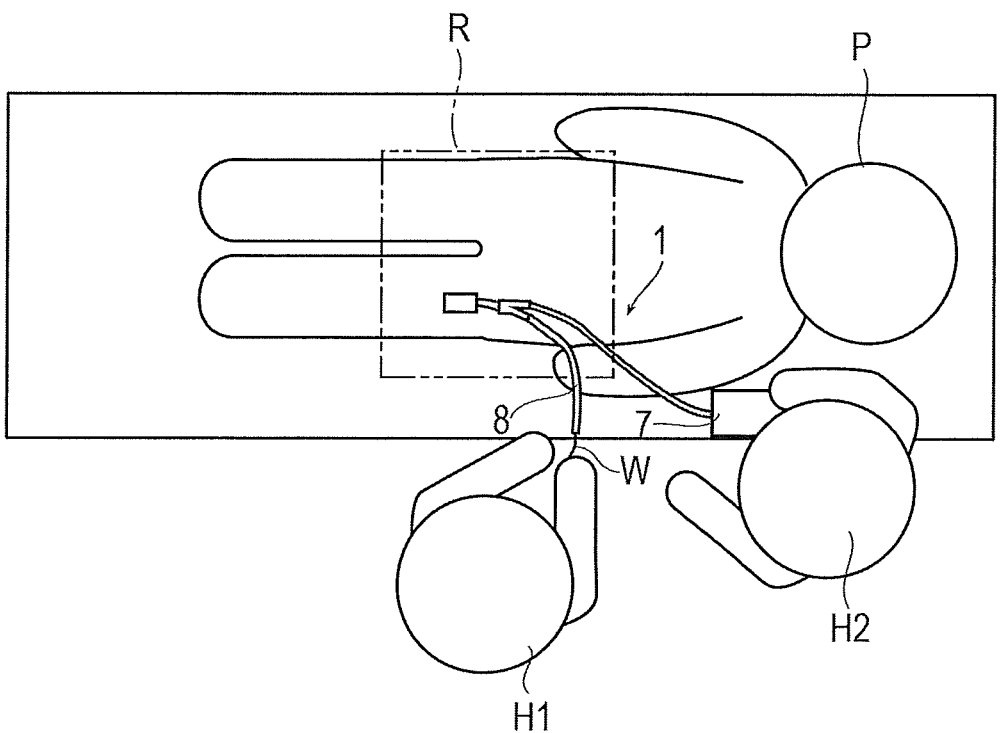

In contrast, in the illustrated embodiment representing an example of the disclosed medical device, as illustrated in FIG. 7(B), the distance between a position where the operator H1 operates the guide wire W by the medical tube 8 and the lesion area may be extended. Accordingly, since the operator H1 can work outside the range R in which the amount of irradiation of the X-ray is relatively high, it is possible to suppress the operator H1 from being exposed to the X-ray during work.

Further, since the operator H1 can select a desired working position by adjusting the length of the medical tube 8, the operator H1 does not need to work in an unreasonable posture and thus a burden on the operator H1 can be reduced. Further, since a range of a position where the operator H1 can work by the medical tube 8 is widened even when the position of the external drive apparatus 7 is fixed, the workability can be improved.

Furthermore, in the medical device 1 according to the embodiment, the other operator H2 holds the external drive apparatus 7 in a fixed state while the operator H1 operates the guide wire W. Since a distance between the operator H1 and the other operator H2 can be adjusted in accordance with the adjustment of the working position of the operator H1 using the medical tube 8, a work can be smoothly performed without any interference during the work.

In order to improve the workability of the operator H1, for example, a method of increasing the length of the guide wire lumen 26 of the medical device 1 without using the medical tube 8 as in the embodiment may be considered. However, when the length of the guide wire lumen 26 is extended, the length of the guide wire W also needs to be extended. When the length of the guide wire W is extended, a friction force against the guide wire lumen 26 increases so that the guide wire W does not move easily or the transmission of power such as pushing or rotating by the operation from the proximal side of the operator H1 becomes difficult. Accordingly, the workability of the operator H1 is degraded.

Next, at step S6, the drive shaft 42 is rotated by the drive unit 71 so that the ultrasound transducer 411 is radially scanned and a tomographic image of a biological tissue including a lesion area is acquired.

When the directions of the tomographic image and the angiographic image are aligned to each other by checking a positional relation of the guide wire W and the oscillator unit 41 using both the tomographic image and the angiographic image, the guide wire W can be efficiently moved to a position of the lesion area which is seen by the tomographic image.

Next, at step S7, the medical device 1 is removed from the blood vessel while the guide wire W is left inside the blood vessel.

Figure 8A:
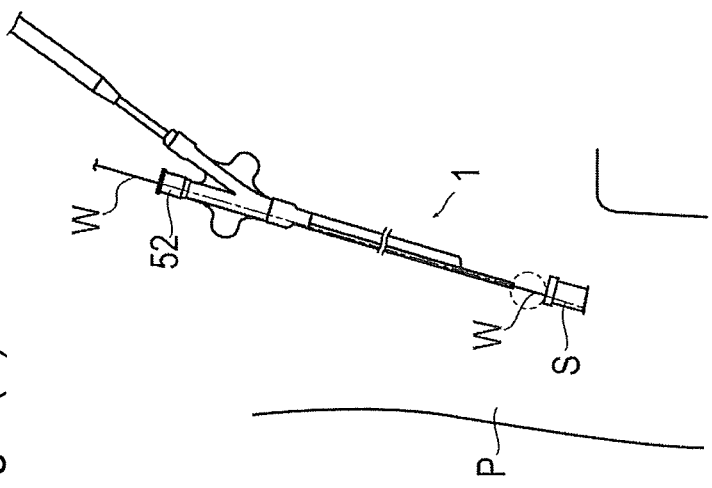
FIGS. 8(A) to 8(C) are diagrams illustrating an operation of removing the medical device according to the embodiment.
Figure 8B:
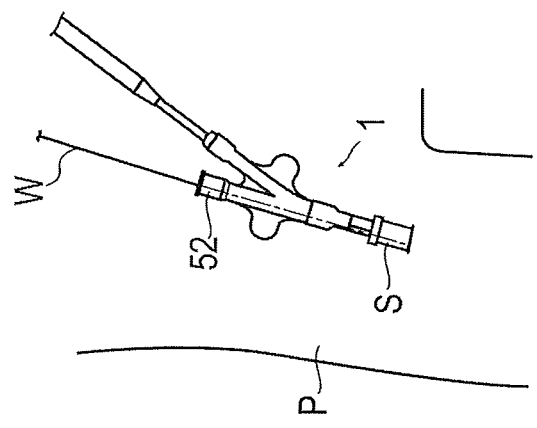
Figure 8C:
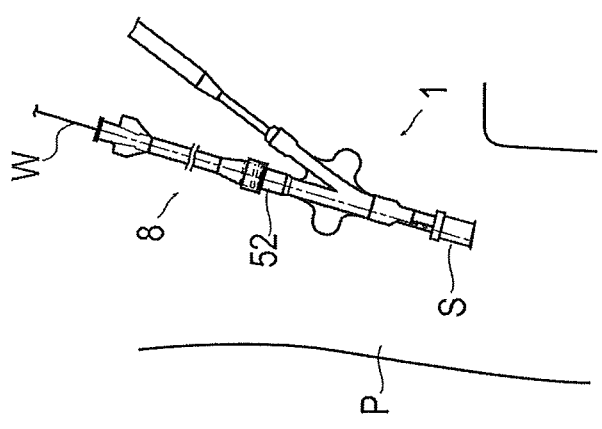

To accomplish this, the medical tube 8 is first separated from the second hub portion 52 from the state illustrated in FIG. 8(A) to achieve the state illustrated in FIG. 8(B). Next, as illustrated in FIG. 8(C), the medical device 1 is pulled to the proximal side or in the proximal direction along the guide wire W and the medical device 1 is separated from the guide wire W. Subsequently, a treatment catheter device is inserted into a blood vessel along the guide wire W.

Since the medical tube 8 is separated from the second hub portion 52 as illustrated in FIG. 8(B) when the medical device 1 is removed from the blood vessel, the length of the guide wire W that is exposed to the proximal side of the medical device 1 is increased by the length L of the medical tube 8 (see FIG. 4(A)). By virtue of the increased exposure length of the guide wire W, a distance in which the medical device 1 can move toward the proximal side along the guide wire W increases.

For this reason, an exposure portion of the guide wire W also remains at the proximal side of the second hub portion 52 when the medical device 1 is drawn to the proximal side until a state where the guide wire W is exposed to a gap (a portion surrounded by a dashed line in FIG. 8(C)) between the guiding sheath S and the distal portion of the medical device 1 (the shaft portion 2) is confirmed as illustrated in FIG. 8(C). Accordingly, when the medical device 1 is drawn to the proximal side or moved in the proximal direction along the guide wire W while the guide wire W exposed to the distal side of the medical device 1 is gripped, the medical device 1 can be easily separated. In this way, since the medical tube 8 is separated, the medical device 1 can be relatively easily removed even when the relatively short guide wire W is used. By using the relatively short guide wire W, the operability of the guide wire W can be improved.

After the medical device 1 is removed from the blood vessel, a replacement operation of inserting a medical device different from the medical device 1 into the blood vessel along the guide wire W can be performed.

Additionally, a timing of attaching and detaching the medical tube 8 is not limited to the above-described timing and the medical tube 8 can be attached and detached at a timing desired by the operator if necessary.

In this way, a treatment method using the medical device 1 according to the illustrated embodiment representing an example of the disclosed treatment method is a treatment method using the medical tube 8 removably attached to the end of the medical device 1 including the guide wire lumen 26 through which the guide wire W is insertable and a medical procedure including a diagnosis or a treatment is performed while adjusting the length of the lumen through which the guide wire W is inserted after the attachment and detachment of the medical tube 8 at the end of the medical device 1.

Further, the medical procedure includes at least one of an operation of inserting the guide wire W through the guide wire lumen 26, an operation of inserting the medical device 1 into the body lumen, an X-ray photographing operation, an operation of acquiring a tomographic image, and an operation of removing the medical device 1 from the body lumen.

Further, the medical procedure includes an operation of attaching the medical tube 8 to the end of the medical device 1 before the X-ray photographing operation.

Further, the medical procedure includes an operation of separating the medical tube 8 from the end of the medical device 1 before the medical device 1 is removed from the body lumen.

Further, the medical procedure includes an operation of inserting the other medical device into the body lumen along the guide wire W after the medical device 1 is removed from the body lumen.

Further, the medical device 1 includes at least one of an image diagnosis catheter, a micro catheter, a guiding catheter, a balloon catheter, a self-expanding stent delivery system, a balloon expandable stent delivery system, a contrast catheter, an atherectomy catheter, an endoscope catheter, and a medical solution administering catheter.

As described above, the medical tube 8 according to the illustrated embodiment representing an example of the disclosed medical device includes the first connection portion 81 (the connection portion) which is removably attached to the second hub portion 52 (the end of the catheter) connected to the second shaft proximal portion 223 of the shaft portion 2 including the guide wire lumen 26 through which the guide wire W is insertable and the tube main body 83 which includes a lumen 83a through which the guide wire W is insertable and the lumen 83a communicates with the guide wire lumen 26 while being attached to the second hub portion 52 through the first connection portion 81.

Further, the medical device 1 according to the embodiment includes the imaging sheath 61 which includes the imaging lumen 25, the guide wire sheath 62 which includes the guide wire lumen 26 disposed in parallel to the imaging lumen 25 and allowing the guide wire W to be insertable therethrough, the second hub portion 52 (the hub portion) which is connected to the proximal end of the guide wire sheath 62, the oscillator unit 41 (the imaging unit) which is fixed to the distal end of the drive shaft 42 and is able to acquire image information, and the medical tube 8 which includes the first connection portion 81 (the connection portion) removably attached to the second hub portion 52 and the tube main body 83 including the lumen 83a allowing the guide wire W to be insertable therethrough. In a state where the medical tube 8 is attached to the second hub portion 52 through the first connection portion 81, the lumen 83a communicates with the guide wire lumen 26.

According to the medical tube 8 or the medical device 1, it is possible to flexibly adjust the working position of the operator H1 of the guide wire W using the medical tube 8. Accordingly, the workability of the operator H1 can be improved. Further, it is possible to perform work at a position where the amount of irradiation of the X-ray is relatively low when photographing the lesion area of the patient P through an X-ray by adjusting the working position using the medical tube 8. For this reason, the amount of exposure of the X-ray to the operator H1 can be reduced.

First Modified Example of Medical Tube

Referring to FIGS. 9(A) and 9(B), a medical tube 800 according to a first modified example is described. This medical tube 800 is different from the above-described embodiment in that a plurality of tube main bodies are connectable by a first connection portion and a second connection portion. In this modified example shown in FIGS. 9(A) and 9(B), the same reference numerals are used to identify parts having the same functions as those of the above-described embodiments and a description of such features is not repeated.

The medical tube 800 includes, as illustrated in FIG. 9(A), a first medical tube 800a, a second medical tube 800b, and a third medical tube 800c.

The first medical tube 800a includes a first connection portion 801a, a second connection portion 802a, and a tube main body 803a. The second medical tube 800b includes a first connection portion 801b, a second connection portion 802b, and a tube main body 803b. The third medical tube 800c includes a first connection portion 801c, a second connection portion 802c, and a tube main body 803c.

The first connection portions 801a, 801b, and 801c are respectively air-tightly and liquid-tightly connected to the distal portions of the tube main bodies 803a, 803b, and 803c. The first connection portions 801a, 801b, and 801c include the female screw portions 81a in which thread grooves are formed in the inner surfaces of the inner lumens.

The second connection portions 802a, 802b, and 802c are air-tightly and liquid-tightly connected to the proximal portions of the tube main bodies 803a, 803b, and 803c. The second connection portions 802a, 802b, and 802c include the male screw portions 82a in which screw threads are formed in an annular shape.

The axial lengths L1, L2, and L3 of the first medical tube 800a, the second medical tube 800b, and the third medical tube 800c are different from one another and the relationship between the lengths L1, L2, L3 may be L1<L2<L3. A ratio (L1:L2:L3) of the lengths L1, L2, and L3 can be, for example, 1:2:3.

Additionally, since the axial lengths of the first connection portions 801a, 801b, and 801c are the same and the axial lengths of the second connection portions 802a, 802b, and 802c are the same, the relationship between the lengths of the tube main bodies 803a, 803b, and 803c may also be L11<L12<L13.

As illustrated in FIG. 9(B), each of the male screw portion 521 of the second hub portion 52 and the male screw portions 82a of the second connection portions 802a, 802b, and 802c can be threaded into the female screw portion 81a. Accordingly, the axial length of the medical tube 800 connected to the second hub portion 52 can be, for example, L1+L2+L3 by connecting all of the first medical tube 800a, the second medical tube 800b, and the third medical tube 800c, can be L1+L2 by connecting only the first medical tube 800a and the second medical tube 800b, or can be L1+L3 by connecting only the first medical tube 800a and the third medical tube 800c. In this way, the length of the medical tube 800 connected to the second hub portion 52 can be adjusted in more detail by changing the combination of the first medical tube 800a, the second medical tube 800b, and the third medical tube 800c.

As described above, the medical tube 800 according to the first modified example includes the first connection portions 801a, 801b, and 801c and the tube main bodies 803a, 803b, and 803c and the first connection portions 801a, 801b, and 801c are connectable to the plurality of tube main bodies 803a, 803b, and 803c. Accordingly, the length of the medical tube 800 can be adjusted to a length desired by the operator.

Further, the axial lengths of the plurality of tube main bodies 803a, 803b, and 803c are different. The length of the medical tube 800 can be adjusted in more detail by appropriately changing the combination of the plurality of tube main bodies 803a, 803b, and 803c.

Additionally, in the first modified example, a configuration has been described in which the medical tube 800 includes three tube main bodies 803a, 803b, and 803c, three second connection portions 802a, 802b, and 802c, and three tube main bodies 803a, 803b, and 803c, but the number of the connection portions and the tube main bodies is not limited thereto. Further, the lengths of the plurality of tube main bodies may be the same.

Second Modified Example of Medical Tube

Figure 10A:
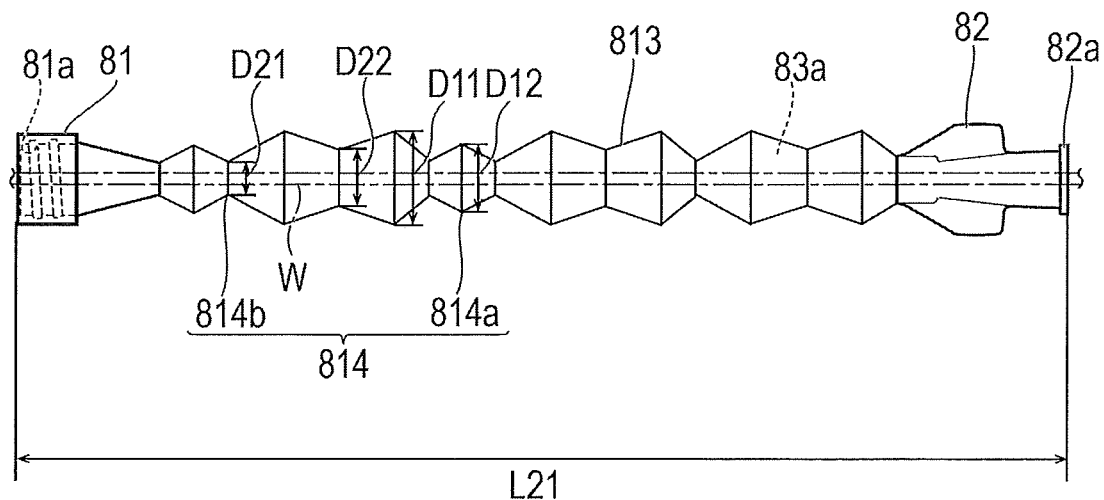
FIG. 10(A) is a plan view illustrating a medical tube according to a second modified example and FIG. 10(B) is a plan view illustrating a state where the medical tube illustrated in FIG. 10(A) is contracted in the axial direction.
Figure 10B:
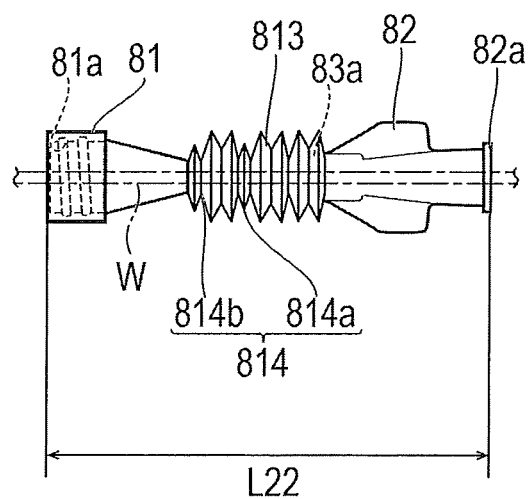

Referring to FIGS. 10(A) and 10(B), a medical tube 810 according to a second modified example is described. The medical tube 810 is different from the above-described embodiments in that a tube main body 813 includes a bellows shaped portion 814 with a bellows box structure. In addition, in this modified example shown in FIGS. 10(A) and 10(B), features that are the same as features in the above-described embodiments and that have the same function as those of the above-described embodiments are identified by the same reference numbers and a detailed description of such features is not repeated.

The tube main body 813 includes, as illustrated in FIG. 10(A), the bellows shaped portion 814 which includes a mountain portion (mountain portions) 814a protruding outward in the radial direction and a valley portion (valley portions) 814b recessed inward in the radial direction in relation to the mountain portion 814a. As illustrated in FIG. 10(B), it is possible to shorten the axial length of the medical tube 810 from the length L21 to the length L22 by folding (axially compressing) the bellows shaped portion 814.

When the cross-sectional shape of the bellows shaped portion 814 is substantially circular, at least a part of the adjacent mountain portions 814a have different outer diameters D11 and D12. Further, at least a part of the adjacent valley portions 814b have different outer diameters D21 and D22. Accordingly, when the bellows shaped portion 814 is folded or axially collapsed, it is possible to more largely extend and contract the length of the tube main body 813 compared to a case where the outer diameters of the mountain portions and the outer diameters of the valley portions are respectively the same. For this reason, the tube main body 813 can be folded (axially shortened) and extended (axially lengthened).

In addition, at least a part of the outer diameters of the adjacent mountain portions 814a may be different and the outer diameters of the valley portions 814b may be the same. In contrast, at least a part of the outer diameters of the adjacent valley portions 814b may be different and the outer diameters of the mountain portions 814a may be the same.

Further, a position of the bellows shaped portion 814 in the tube main body 813 is not particularly limited as long as the bellows shaped portion is formed in at least a part of the tube main body 813, but is desirably formed in the vicinity of the first connection portion 81. Further, the cross-sectional shape of the bellows shaped portion 814 is not limited to a substantially circular shape and may be, for example, a polygonal shape.

As described above, in the medical tube 810 according to the second modified example, the tube main body 813 includes the bellows shaped portion 814 which includes the mountain portion 814a protruding outward in the radial direction and the valley portion 814b recessed inward in the radial direction in relation to the mountain portion 814a. Accordingly, it is possible to shorten the axial length of the tube main body 813 by folding or axially collapsing the bellows shaped portion 814. For this reason, it is possible to perform an operation of replacing the medical device 1 without performing an operation of separating the medical tube 810 from the second hub portion 52. Accordingly, since it is possible to omit a trouble of an operation of separating the medical tube 810 from the second hub portion 52, it is possible to efficiently perform an operation.

Third Modified Example of Medical Tube

Figure 11A:
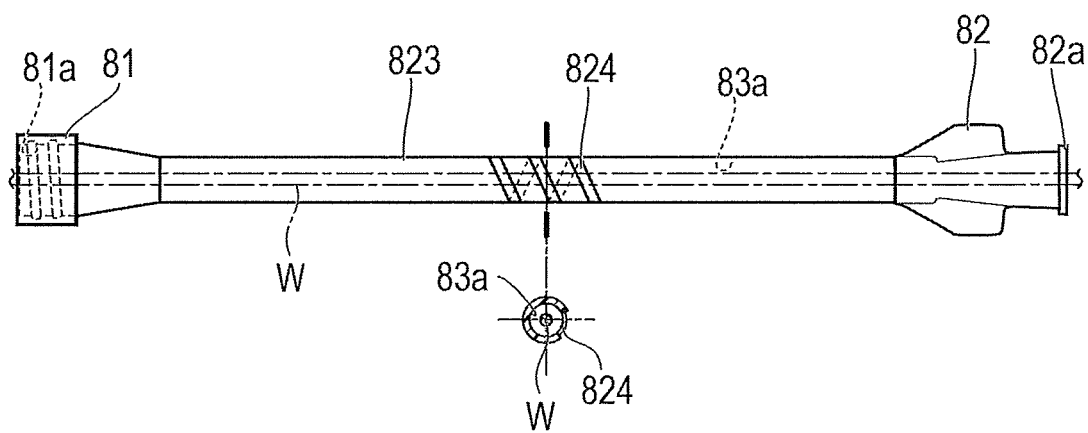
FIG. 11(A) is a plan view illustrating a medical tube according to a third modified example and FIG. 11(B) is a plan view illustrating a state where a force in the twisting direction is applied to the medical tube illustrated in FIG. 11(A).
Figure 11B:
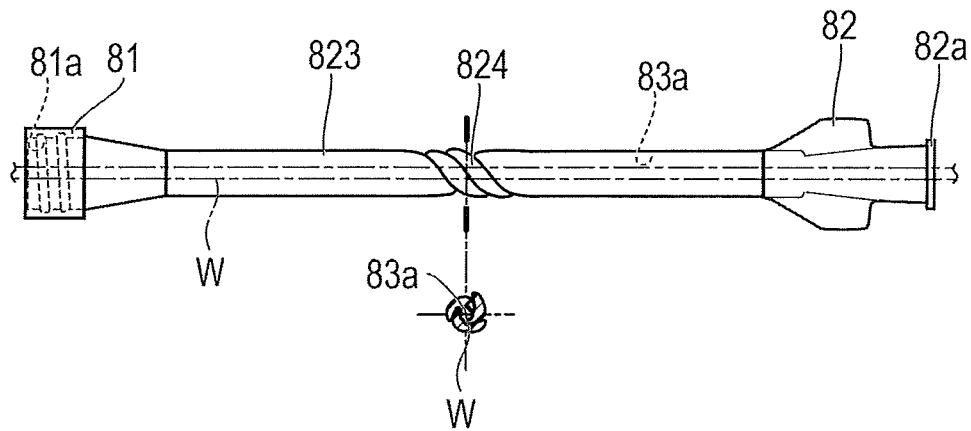

Referring to FIGS. 11(A) and 11(B), a medical tube 820 according to a third modified example is described. The medical tube 820 according to this third modified example is different from the above-described embodiments in that the tube main body 823 includes a deformation portion 824. In addition, in this modified example shown in FIGS. 11(A) and 11(B), features that are the same as features in the above-described embodiments and that have the same function as those of the above-described embodiments are identified by the same reference numbers and a detailed description of such features is not repeated.

The tube main body 823 includes, as illustrated in FIG. 11(A), the deformation portion 824 which is deformable in a direction in which the diameter of the lumen 83a decreases. The deformation portion 824 is thinner than the other portions and is formed in a spiral shape in the axial direction. Since the deformation portion 824 is more easily deformed compared to the other portions, when a force in the twisting direction is applied to the tube main body 823, the deformation portion 824 is twisted so that a part of the diameter of the lumen 83a decreases as illustrated in FIG. 11(B). Accordingly, the tube main body 823 can hold the guide wire W in a predetermined range.

Additionally, the deformation portion 824 is not limited to the above-described configuration as long as the deformation portion can be deformed in a direction in which the diameter of the lumen 83a decreases.

As described above, the medical tube 820 according to the third modified example includes the deformation portion 824 which is deformable in a direction in which the diameter of the lumen 83a decreases. Accordingly, the operator can easily hold the guide wire W by deforming the deformation portion 824. When the guide wire W is pushed into the body lumen in a held state, it is possible to sufficiently transmit a pushing force to the distal end of the guide wire W when the blocked lesion area is perforated by the guide wire W. Further, when the guide wire W having a curved distal end is used, it is possible to maintain the circumferential directionality of the guide wire W so that the curved portion of the distal end of the guide wire W faces a branched or meandered portion inside the body lumen. Accordingly, the guide wire W can move forward in a desired direction when the guide wire W moves forward inside the branched or meandered body lumen.

Fourth Modified Example of Medical Tube

Figure 12A:
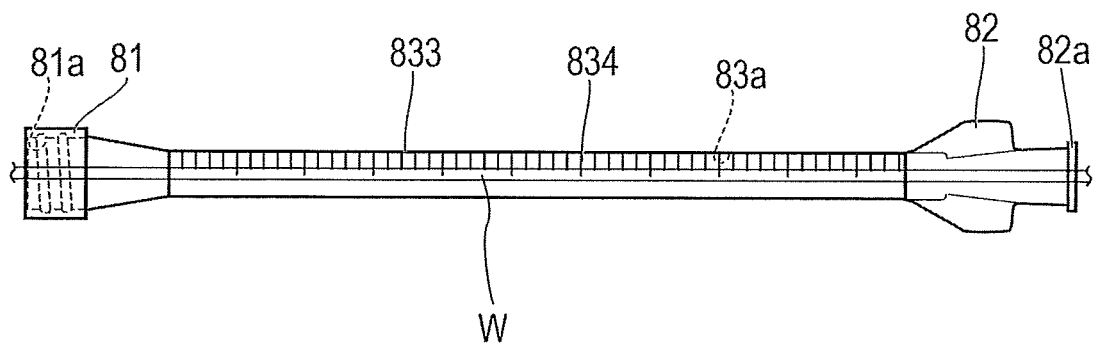
FIG. 12(A) is a plan view illustrating a medical tube according to a fourth modified example and FIGS. 12(B) and 12(C) are partial cross-sectional views illustrating a case where a size of a lesion area is measured by using the medical tube and a guide wire illustrated in FIG. 12(A).
Figure 12B:
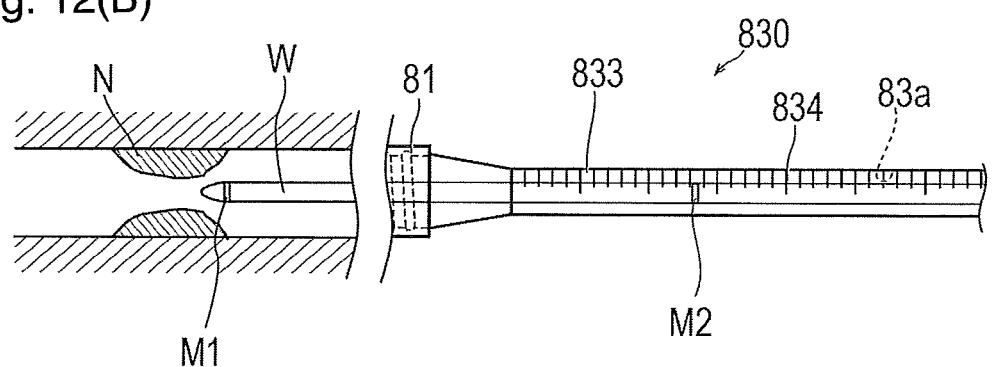
Figure 12C:
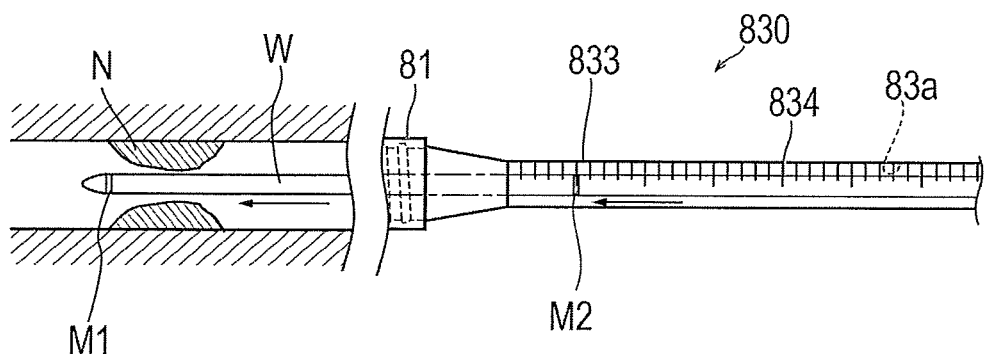

Referring to FIGS. 12(A) to 12(C), a medical tube 830 according to a fourth modified example is described. The medical tube 830 according to this fourth modified example is different from the above-described embodiments in that the inside of the lumen 83a is visible from the outside of a tube main body 833. In addition, in this modified example shown in FIGS. 12(A)-12(C), features that are the same as features in the above-described embodiments and that have the same function as those of the above-described embodiments are identified by the same reference numbers and a detailed description of such features is not repeated.

The tube main body 833 is formed of a transparent material or a translucent material which allows the inside of the lumen 83a to be visible from the outside. Since the medical tube 830 is disposed at the outside of the body, the guide wire W inside the lumen 83a can be visually checked from the outside.

The tube main body 833 includes grids 834 which are provided at a predetermined interval in the axial direction as illustrated in FIG. 12(A). For example, as illustrated in FIG. 12(B), an X-ray contrast marker M1 is provided at the distal portion of the guide wire W and a marker M2 is provided at the proximal portion. As illustrated in FIG. 12(C), the guide wire W is operated so that the X-ray contrast marker M1 moves from the proximal end of the lesion area N to the distal end. At this time, the movement distance of the X-ray contrast marker M1 can be visibly checked at the proximal side by the marker M2 and the grid 834. Accordingly, the axial length of the lesion area N can be relatively simply measured.

The guide wire lumen 26 and the lumen 83a are connected without a check valve from the inside of the body lumen to the outside of the body. Since a pressure inside the body lumen is higher than that of the outside of the body, there is a possibility that blood may flow reversely in the lumen 83a. When blood flows reversely in the lumen 83a, there is a case where a thrombus may be formed in the lumen 83a due to a residue remaining in the lumen 83a.

Since the tube main body 833 according to the fourth modified example is formed of a material allowing the inside of the lumen 83a to be visible from the outside, the reverse flow of blood can be checked from the outside. For this reason, it is possible to suppress a thrombus by performing a treatment for the reverse flow of blood in such a manner that a flush solution flows into the lumen 83a at the time of checking the reverse flow of blood. Further, the degree of the reverse flow of blood can be checked by the grid 834 of the tube main body 833.

As described above, at least a part of the tube main body 833 of the medical tube 830 according to the fourth modified example is formed of a material allowing the inside of the lumen 83a to be visible from the outside. Accordingly, it is possible to check the reciprocating length of the guide wire W or to visibly check the reverse flow of blood inside the lumen 83a. Accordingly, the operability can be further improved.

Fifth Modified Example of Medical Tube

Figure 13A:
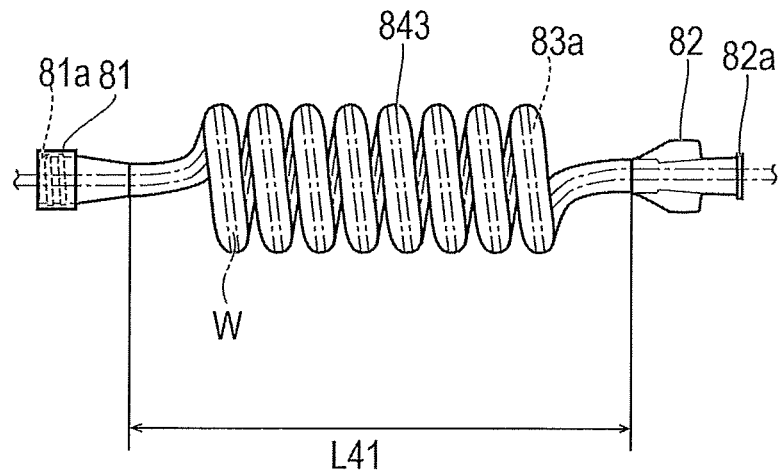
FIG. 13(A) is a plan view illustrating a medical tube according to a fifth modified example and FIG. 13(B) is a plan view illustrating a state where the medical tube illustrated in FIG. 13(A) is extended in the axial direction.
Figure 13B:
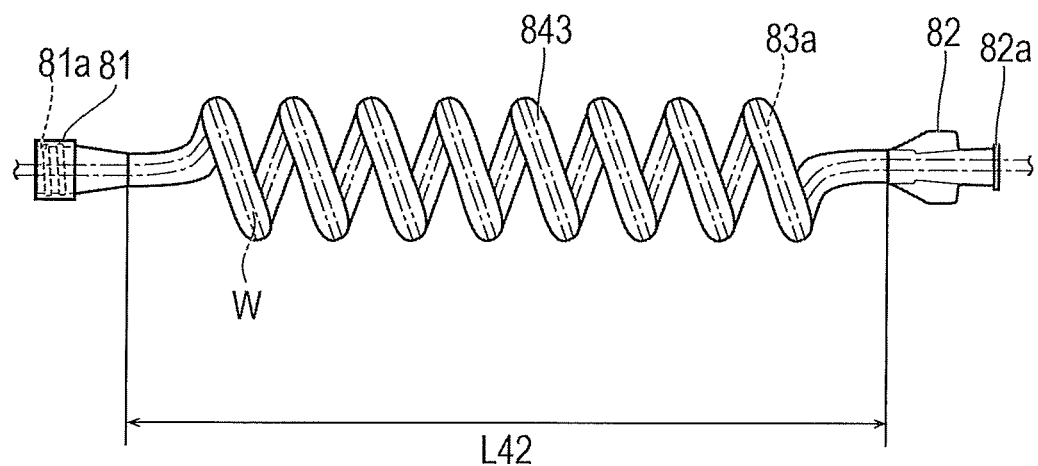

Referring to FIGS. 13(A) and 13(B), a medical tube 840 according to a fifth modified example is described. The medical tube 840 is different from the above-described embodiments in that the tube main body 843 is wound in a spiral shape. In addition, in this modified example shown in FIGS. 13(A) and 13(B), features that are the same as features in the above-described embodiments and that have the same function as those of the above-described embodiments are identified by the same reference numbers and a detailed description of such features is not repeated.

The tube main body 843 has flexibility and is wound in a spiral shape as illustrated in FIG. 13(A). When a pulling force is applied to the tube main body 843 in the axial direction, the axial length of the tube main body 843 increases from the length L41 to the length L42 as illustrated in FIG. 13(B). When the pulling force in the axial direction is released, the axial length of the tube main body 843 decreases from the length L42 to the length L41 as illustrated in FIG. 13(A).

As described above, the tube main body 843 of the medical tube 840 according to the fourth modified example has flexibility and is wound in a spiral shape. Accordingly, it is possible to adaptively adjust the length of the tube main body 843 in accordance with a distance between the patient and the operator.

While the inventive medical tube and medical device disclosed here have been described above by way of the described embodiment and the modified examples representing examples of the inventive medical tube and medical device, the invention is not limited to the described configurations.

For example, in the above-described embodiment, a case has been described in which the invention is applied to the image diagnosis catheter used in an intra vascular ultra sound (IVUS) for acquiring a diagnosis image used to diagnose a lesion area inside a living body, but can be applied to an image diagnosis catheter for acquiring an image using light according to an optical coherence tomography (OCT) or a hybrid type (dual type) image diagnosis catheter usable for both IVUS and OCT. Further, the invention is not limited to the image diagnosis catheter and can be widely applied to a catheter including a guide wire lumen such as a micro catheter.

Further, in the above-described embodiment, the first connection portion of the medical tube is attached to and detached from the second hub portion of the hub by a thread structure, but the invention is not limited thereto. The attachment and detachment may be performed by other mechanical structures such as an attachable/detachable fitting structure.

Further, the drive shaft may be movable inside the imaging lumen in the axial direction. Accordingly, it is possible to perform a pull-back operation in which the imaging unit disposed at the distal end of the drive shaft rotates while moving in the axial direction. By performing the pull-back operation, it is possible to scanningly obtain a tomographic image of 360° to an arbitrary position in a surrounded tissue body inside the body lumen in the axial direction.

Further, the medical device that employs the medical tube according to the invention is not limited to the image diagnosis catheter and, for example, a micro catheter, a guiding catheter, a balloon catheter, a self-expanding stent delivery system, a balloon expandable stent delivery system, a contrast catheter, an atherectomy catheter, an endoscope catheter, and a medical solution administering catheter can be employed.

The detailed description above describes a medical tube and medical device. The invention is not limited, however, to the precise embodiment, modified examples and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical tube comprising:
 a connection portion that is removably attached to an end of a catheter, the catheter including a guide wire lumen through which is insertable a guide wire;
 a tube main body that includes a lumen through which is insertable the guide wire, the connection portion being provided at one end of the tube main body;
 the tube main body including a bellows shaped portion which includes a mountain portion protruding outward in a radial direction and a valley portion recessed inward in the radial direction in relation to the mountain portion; and
 the lumen in the tube main body communicating with the guide wire lumen through the connection portion.

2. The medical tube according to claim 1,
 wherein the connection portion is one of a plurality of connection portions and the tube main body is one of a plurality of tube main bodies, each of the connection portions being provided at one end of one of the tube main bodies, and
 the connection portions being configured to connect the plurality of tube main bodies to one another.

3. The medical tube according to claim 2, wherein axial lengths of the plurality of tube main bodies are different from one another.

4. The medical tube according to claim 1, wherein the tube main body includes a deformation portion which is deformable in a direction in which a diameter of the lumen in the tube main body decreases.

5. The medical tube according to claim 1, wherein at least a part of the tube main body is formed of a material allowing the inside of the lumen to be visible from an outside.

6. A medical device that acquires an image while positioned in a body lumen, the medical device comprising:
 an imaging sheath that includes an imaging lumen into which a rotatable drive shaft is insertable;
 a guide wire sheath that includes a guide wire lumen which is disposed in parallel to the imaging lumen and through which a guide wire is insertable;
 a hub portion connected to a proximal end of the guide wire sheath;
 a first medical tube that includes a first connection portion removably attached to the hub portion, a second connection portion and a tube main body integral with both the first connection portion of the first medical tube and the second connection portion of the first medical tube, the tube main body of the first medical tube including a lumen through which the guide wire is insertable;
 a second medical tube comprised of a first connection portion and a tube main body, the tube main body of the second medical tube including a lumen that passes through the tube main boy of the second medical tube;
 the first connection portion of the second medical tube being removably connected to the second connection portion of the first medical tube; and
 the lumen of the first tube main body communicating with the guide wire lumen while the first connection portion of the first medical tube is attached to the hub portion.

7. The medical device according to claim 6, wherein the first medical tube possesses a first length extending between opposite ends of the first medical tube, the second medical tube possessing a second length extending between opposite ends of the second medical tube, the first length being different from the second length.

8. The medical device according to claim 6, wherein the tube main body possesses a shape that includes a plurality of mountain portions each protruding outward in a radial direction and a plurality of valley portions recessed inward in the radial direction in relation to the mountain portions, the valley portions alternating with the mountain portions along an axial extent of the tube main body.

9. The medical device according to claim 6, wherein the tube main body of at least one of the first medical tube and the second medical tube includes a deformation portion configured to deform in a direction in which a diameter of the lumen in the tube main body of the at least one of the first medical tube and the second medical tube decreases.

10. The medical device according to claim 6, wherein at least a part of the tube main body of at least one of the first medical tube and the second medical tube is formed of a material allowing an inside of the lumen to be visible from outside the tube main body of the at least one of the first medical tube and the second medical tube.

11. The medical device according to claim 6, wherein the tube main body of at least one of the first medical tube and the second medical tube is wound in a spiral shape and is flexible to permit an axial length of the tube main body of the at least one of the first medical tube and the second medical tube to be increased.

12. A method comprising:
   introducing a guide wire that is positioned in a blood vessel into an open distal end of a medical device and moving the medical device in a distal direction along the guide wire that is positioned in the blood vessel so that the medical device is introduced into the blood vessel and the guide wire moves along a guide wire lumen in the medical device, the medical device comprising a hub through which the guide wire lumen passes, the hub including a hub portion through which the guide wire lumen passes, the hub portion including a proximal end, and a medical tube removably connected to the proximal end of the hub portion, the medical tube including a lumen that communicates with the guide wire lumen passing through the hub portion;
   advancing the medical device along the guide wire to cause the guide wire to pass through the guide wire lumen in the hub and the hub portion;
   further advancing the medical device along the guide wire to cause the guide wire to pass through the lumen in the medical tube so that the guide wire projects proximally beyond a proximal end of the medical tube so that the guide wire is located outside the medical tube; and
   disconnecting the medical tube from the hub portion so that the medical tube is separated from the hub portion, and then moving the medical tube in a proximal direction relative to the guide wire to remove the medical tube from the guide wire while the medical device remains in the blood vessel.

13. The method according to claim 12, wherein the medical device is introduced into the blood vessel through a guiding sheath, the method further comprising moving the medical device in the proximal direction relative to the guide wire after removing the medical tube from the guide wire.

14. The method according to claim 13, wherein the moving of the medical device in the proximal direction relative to the guide wire includes moving the medical device in the proximal direction so that a distal end of the medical device is positioned proximally of a proximal end of the guiding sheath so that a gap exists between the distal end of the medical device and the proximal end of the guiding sheath and so that the guide wire is exposed in the gap, the method further comprising gripping the guide wire exposed in the gap while the guidewire is located in the guide wire lumen of the medical device, and holding the guidewire while moving the medical device in the proximal direction to separate the medical device from the guide wire.

15. The method according to claim 12, further comprising changing an axial length of the medical tube.

* * * * *